United States Patent
Song et al.

(10) Patent No.: US 8,911,681 B2
(45) Date of Patent: Dec. 16, 2014

(54) WETNESS INDICATOR HAVING VARIED HUES

(75) Inventors: Xuedong Song, Alpharetta, GA (US); Karen Meloy Goeders, Atlanta, GA (US); Ning Wei, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 594 days.

(21) Appl. No.: 13/230,102

(22) Filed: Sep. 12, 2011

(65) Prior Publication Data
US 2013/0066289 A1 Mar. 14, 2013

(51) Int. Cl.
| | | |
|---|---|---|
| *G01N 21/75* | (2006.01) | |
| *A61L 15/56* | (2006.01) | |
| *G01N 33/50* | (2006.01) | |
| *G01N 21/78* | (2006.01) | |
| *G01N 33/52* | (2006.01) | |
| *G01N 31/22* | (2006.01) | |
| *B01L 3/00* | (2006.01) | |
| *G01N 30/88* | (2006.01) | |
| *G01N 33/18* | (2006.01) | |

(52) U.S. Cl.
CPC .............. *A61L 15/56* (2013.01); *G01N 33/50* (2013.01); *G01N 21/78* (2013.01); *G01N 33/52* (2013.01); *G01N 33/525* (2013.01); *B01L 2300/0816* (2013.01); *G01N 31/22* (2013.01); *G01N 31/222* (2013.01); *B01L 3/5023* (2013.01); *G01N 30/88* (2013.01); *G01N 33/18* (2013.01)
USPC ........... 422/421; 422/400; 422/401; 422/420; 422/422; 422/423; 422/424; 422/425; 422/426; 422/427; 422/428; 422/429; 422/68.1; 422/82.05; 422/82.06; 436/164; 436/169; 436/170; 435/13; 435/283.1; 435/287.1; 435/287.7; 435/287.8; 435/287.9; 435/288.7

(58) Field of Classification Search
CPC ....... G01N 21/78; G01N 30/88; G01N 31/22; G01N 33/18; G01N 33/50; G01N 31/222; G01N 33/52; G01N 33/525; B01L 2300/0816; B01L 3/5023; A61L 15/56
USPC ......... 422/400, 401, 420, 421, 422, 423, 424, 422/425, 426, 427, 428, 429, 68.1, 82.05, 422/82.06; 436/164, 169, 170; 435/13, 435/283.1, 287.1, 287.7, 287.8, 287.9, 435/288.7
See application file for complete search history.

(56) References Cited

U.S. PATENT DOCUMENTS

| 4,163,039 A | 7/1979 | Emrich |
| 4,287,153 A | 9/1981 | Towsend |

(Continued)

FOREIGN PATENT DOCUMENTS

| JP | 2000-279442 A | 10/2000 |
| JP | 2007-175390 A | 7/2007 |

(Continued)

OTHER PUBLICATIONS

"CIE Publication No. 15.2," *Colorimetry*, Second Edition, 1986, pp. 1-74.

(Continued)

*Primary Examiner* — Dennis M White
(74) *Attorney, Agent, or Firm* — Denise L. Stoker

(57) ABSTRACT

A wetness indicator material may be used on a substrate to form a wetness sensor. The sensor may show either the presence or absence of an aqueous-based fluid or water-containing medium, such as vaginal fluid or urine in a personal hygiene article. The wetness sensor may be incorporated into the article. The wetness indicator material includes a standard colorant that does not change color when wetted. The standard colorant increases the range of hues exhibited by the wetness indicator material.

17 Claims, 6 Drawing Sheets

(56) References Cited

U.S. PATENT DOCUMENTS

| | | | |
|---|---|---|---|
| 4,798,603 | A | 1/1989 | Meyer et al. |
| 4,801,494 | A | 1/1989 | Datta et al. |
| 4,908,026 | A | 3/1990 | Sukiennik et al. |
| 5,057,154 | A | 10/1991 | Kusakata et al. |
| 5,130,290 | A | 7/1992 | Tanimoto |
| 5,197,958 | A | 3/1993 | Howell |
| 5,248,309 | A | 9/1993 | Serbiak et al. |
| 5,417,749 | A | 5/1995 | Krishnan et al. |
| 6,542,379 | B1 | 4/2003 | Lauffer et al. |
| 7,883,997 | B2 | 2/2011 | Yoshida |
| 2006/0229578 | A1* | 10/2006 | Roe et al. ............ 604/361 |
| 2007/0156106 | A1 | 7/2007 | Klofta et al. |
| 2007/0270773 | A1 | 11/2007 | Mackey |
| 2008/0021429 | A1 | 1/2008 | Klofta et al. |
| 2009/0157024 | A1 | 6/2009 | Song |
| 2009/0157025 | A1 | 6/2009 | Song et al. |
| 2009/0275908 | A1 | 11/2009 | Song |
| 2009/0326409 | A1 | 12/2009 | Cohen et al. |
| 2010/0030173 | A1 | 2/2010 | Song et al. |
| 2010/0114047 | A1 | 5/2010 | Song et al. |
| 2010/0262100 | A1 | 10/2010 | Klofta |
| 2011/0015063 | A1 | 1/2011 | Gil et al. |
| 2011/0015597 | A1 | 1/2011 | Gil et al. |
| 2011/0015598 | A1 | 1/2011 | Song et al. |
| 2011/0015599 | A1 | 1/2011 | Song et al. |
| 2011/0144603 | A1 | 6/2011 | Song |
| 2011/0152816 | A1 | 6/2011 | Zhou et al. |
| 2011/0224638 | A1 | 9/2011 | Cohen |

FOREIGN PATENT DOCUMENTS

| | | | |
|---|---|---|---|
| JP | 2007-533417 | A | 11/2007 |
| JP | 2008-054991 | A | 3/2008 |
| JP | 2008-099947 | A | 5/2008 |
| JP | 2010-075464 | A | 4/2010 |
| WO | WO 2007/015523 | A1 | 2/2007 |
| WO | WO 2010/027556 | A1 | 3/2010 |
| WO | WO 2010/117865 | A2 | 10/2010 |
| WO | WO 2011/071807 | A1 | 6/2011 |

OTHER PUBLICATIONS

American Society for Testing Materials (ASTM) Designation: E1164-02, "Standard Practice for Obtaining Spectrometric Data for Object-Color Evaluation," pp. 1-8, published Aug. 2002.

Cost, Frank, "Pocket Guide to Digital Printing," Delmar Publishers, Albany, NY, ISBN 0-8273-7592-1, pp. 144-145.

International Organization for Standardization (ISO) International Standard 7724/1, "Paints and Varnishes—Colorimetry—Part 1: Principles," First edition, 1984, 8 pages.

Japanese Industrial Standard, JIS Z 8722, "Methods of Colour Measurement—Reflecting and Transmitting Objects," 2000, 1-57 and 1 correction page, "Errata."

Morris, Deirdre et al., "Bio-Sensing Textile Based Patch with Integrated Optical Detection System for Sweat Monitoring," *Sensors and Actuators, B: Chemical*, vol. 139, No. 1, May 2009, pp. 231-236.

Schlatter, Sarah, "Bio-sensing textile based patch for sweat monitoring," Biomedical Engineer, University of Rhode Island, viewed online at "http://www.ele.uri.edu/courses/ele482/S09/Sarah_1.pdf" prior to Sep. 12, 2011, 1 page.

* cited by examiner

WETNESS INDICATOR HAVING VARIED HUES

BACKGROUND

The present disclosure pertains to a sensor involving a visual color change due to the presence of an aqueous-based liquid. In particular, the disclosure relates to an a wetness sensor that communicates to a caregiver or user that a personal hygiene article is ready for changing.

Wetness sensing capability in an personal hygiene article, such as an absorbent article, has been a desirable and welcome feature. Disposable absorbent articles such as diapers, training pants, incontinence pads, and the like are highly absorbent and efficiently pull moisture away from the wearer, thereby reducing skin irritation caused by prolonged wetness exposure. However, because these articles are so absorbent, wearers may not realize they have urinated, particularly if they are inexperienced toddlers who may not recognize the meaning of body sensations associated with urination. Thus, the wearer may not recognize their urination control failure or be aware the article should be changed. Furthermore, caregivers may not recognize that the absorbent article requires changing.

Visual mechanisms have been employed to signal the presence of wetness in absorbent articles. There are a large number of wetness sensing technologies that currently exist including electronic-based wetness sensors, color-based wetness sensors, and enzyme-based wetness sensors. However, all those wetness sensing technologies are not ideal and have one or more limitations. For instance, the electronic based wetness sensors are generally too expensive to be disposable, while enzyme-based wetness sensors may have stability issues. Water-soluble dye-based wetness indicators experience dye leaching upon wetting and present blurred graphics.

Thus, a need exists for a wetness sensor that is cost effective, stable and capable of a wide variety of hue changes. A personal hygiene article, in particular an absorbent article, that incorporates such a sensor would be beneficial.

SUMMARY OF THE DISCLOSURE

The present disclosure in accordance with one aspect pertains to a personal hygiene article with a wetness indicator or sensor for detecting the presence of an aqueous-containing media, such as bodily fluids or waste.

In one aspect a sensor is used for detecting the presence of an aqueous-based liquid in a personal hygiene article, the sensor including a substrate having at least one type of wetness indicating material disposed thereon. The wetness indicating material has at least one first colorant that changes color when wetted, and at least one standard colorant that does not change color when wetted. The wetness indicating material exhibits a first hue in a dry state and a different hue in a wet state.

In another aspect a sensor is used for detecting the presence of an aqueous-based liquid in a personal hygiene article. This sensor includes a substrate with a printed layer disposed thereon. The printed layer is made with a color-changing composition that includes a matrix-forming component, a colorant, a standard colorant, a surfactant, and a pH adjuster. The pH adjuster includes a low molecular weight organic acid and a high molecular weight organic acid.

In yet another aspect a sensor is used for detecting the presence of an aqueous-based liquid in a personal hygiene article. The sensor includes a substrate having at least one type of wetness indicating material disposed thereon. The wetness indicating material includes a leuco dye, a developer, a desensitizer, a pH indicator, a pH adjuster and a surfactant. The wetness indicating material exhibits a first hue in a dry state and a different hue in a wet state.

Other features and aspects of the present disclosure are discussed in greater detail below.

Figure 1A:
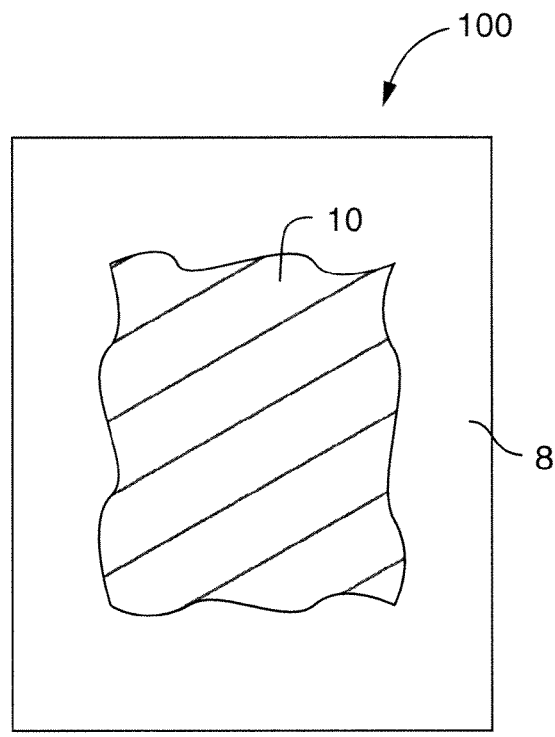
FIGS. 1A-B are schematic representations showing an indicator material applied to a nonwoven substrate according to one aspect of the invention, and the change from one color to another after contact with a water-containing fluid causes a dye to change from colorless to colored.

Repeated use of reference characters in the present specification and drawings is intended to represent same or analogous features or elements of the disclosure.

DETAILED DESCRIPTION OF THE DISCLOSURE

Definitions

The term "hue" as used herein refers to colors such as red, yellow, green, and blue. Different hues are caused by absorption of different wavelengths of light.

The term "value" as used herein refers to a color that is "light" or "dark." Another term for value is "brightness." This property of color tells us how light or dark a color is based on how close it is to white. For instance, canary yellow would be considered lighter than navy blue, which in turn is lighter than black. Therefore, the value of canary yellow is higher than the value of navy blue and black, meaning the canary yellow is lighter in color.

DESCRIPTION

The present disclosure addresses limited options of hue change exhibited by existing wetness indicating technologies (e.g. leuco dyes) which are used to create current wetness indicator graphics or indicia. In contrast to the many existing dye-based indicating materials that transform from colored to colorless or colorless or colored when insulted with a liquid, the indicating materials of the present disclosure have a much wider variety of hue change schemes. A wetness sensor may be made with a pH indicator, a leuco dye, or a combination thereof.

In general, one aspect of the present disclosure pertains to a wetness indicator material that can be used on a substrate to form a wetness sensor. The wetness indicator material shows either the presence or absence of an aqueous-based fluid or water-containing medium, such as vaginal fluid or urine in an absorbent article. The wetness sensor can be incorporated into an absorbent article.

Wetness Sensors Containing at Least One Leuco Dye

In one aspect of the disclosure, the wetness sensor may be made of a substrate and a wetness indicator material which is printed or immobilized on the substrate. In a second aspect, the wetness sensor may be made of substrate and a wetness indicator material made from at least one leuco dye, a developer, a neutral surfactant and a standard colorant such as an organic dye, wherein the leuco dye and the standard colorant are of different or the same hues. In a third aspect, the wetness sensor may be made of a substrate and a wetness indicator material made from at least a leuco dye, a developer, a desensitizer and a standard colorant, wherein the leuco dye and the standard colorant are of the different or the same hues. In a fourth aspect, the wetness sensor may be made of a substrate having two or more layers of wetness indicator material, wherein the first layer of material consists of a leuco dye/desensitizer/developer, and wherein the second layer of material consists of a leuco dye/developer complex. The first layer undergoes color appearance from a colorless state upon wetting while the second layer undergoes discoloration upon wetting. The first layer and the second layer are of different hues. In a fifth aspect of the disclosure, a third layer provides a temporary barrier between the first layer and the second layer.

Figure 1B:
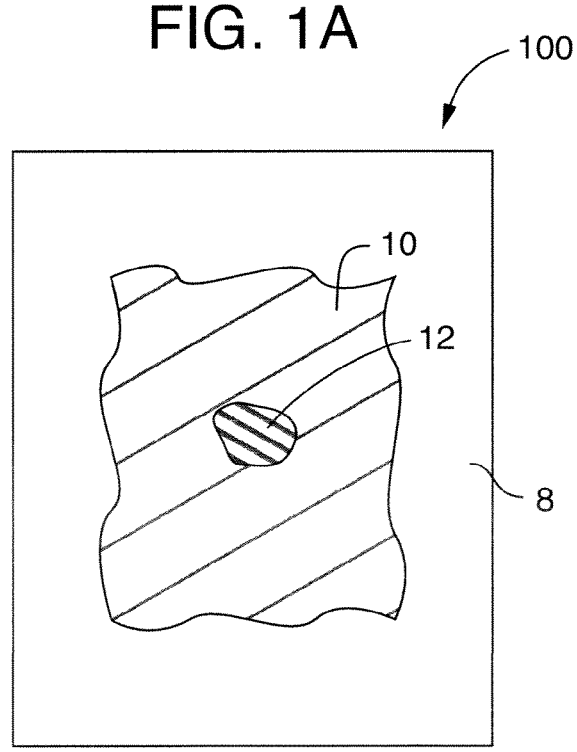

An illustration of one aspect of the present sensor 100 is presented in schematic representations (photographs originally) shown in FIGS. 1A-B. In this aspect, a substrate carries 8 at least one standard colorant having a first hue combined with a wetness indicating material containing at least one leuco dye, at least one desensitizer and at least one developer. An ink binder, solvent and/or viscosity adjustment reagent may also be included in the composition. Desirably, the hue of the standard colorant remains constant before and after being wetted. The initial hue of the indicating material is the same as the standard colorant because the leuco dye is colorless in the dry state. The hue of the leuco dye appears from a colorless state in the presence of a water-based liquid. The hue of the standard colorant combines with the hue of the leuco dye to create a second hue.

For example, in FIG. 1A, the substrate 8 carries a standard colorant that is a first hue (e.g. red) when dry, blended with a leuco dye that is colorless when dry. See color patch 10 (the patch 10 may cover all or a portion of a substrate 10). When the color patch 10 is wetted, the leuco dye turns from a colorless state to a colored state (e.g. blue), and the resulting hue that appears to a viewer is a second hue (e.g. purple), seen as spot 12 in FIG. 1B. It is noted that it is possible in this aspect to show an decrease in value from the first hue as compared to the second hue. In this example, the resulting hue is darker than the initial hue.

Figure 2:
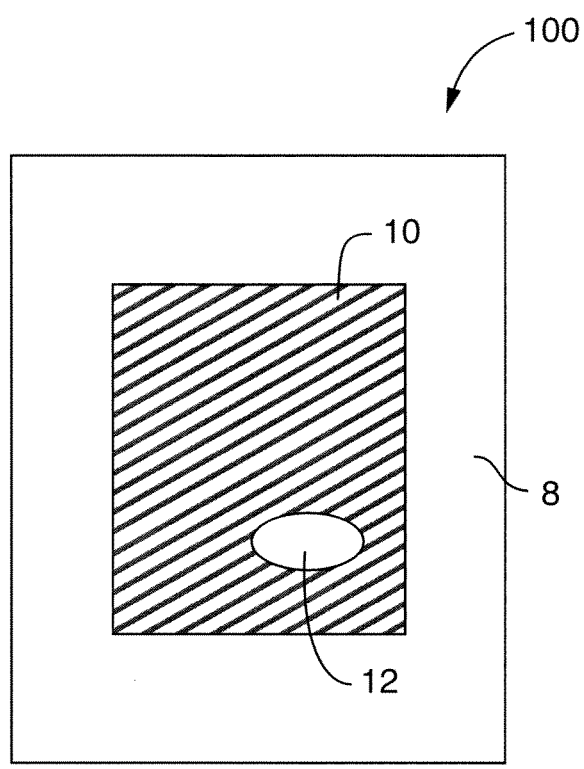
FIG. 2 is a schematic representation showing an indicator material applied to a non-woven substrate according to one aspect of the invention, and the change from one color to another after contact with a water-containing fluid causes a dye to change from colored to colorless.

An illustration of another aspect of the present sensor 100 is presented in the schematic representation (photograph originally) shown in FIG. 2. In this aspect, a substrate 8 carries at least one standard colorant of a first hue combined with an indicating material containing at least one leuco dye of a second hue, at least one developer, and at least one surfactant. The composition is shown as color patch 10. An ink binder, solvent and/or viscosity adjustment reagent may also be included in the composition. Desirably, the standard colorant has a constant hue even when wetted or subjected to a different temperature. Before wetting, an initial hue, which is a combination of a first and second hue, is apparent to the viewer. Upon wetting, the first hue of the standard colorant remains unchanged and the second hue, that of the leuco dye, goes from colored to colorless, or a strong color to a weak color.

For example, in FIG. 1, the substrate 8 carries a standard colorant that is a first hue (e.g. pink) when dry, and a leuco dye that is a second hue (e.g. blue) when dry. The overall color of the sensor 100 is the combination of the first and second hue (e.g. the combination of pink and blue results in purple). When the color patch 10 is wetted, the leuco dye turns colorless, and the resulting hue that appears to a viewer is only the first hue shown as a spot 12 in FIG. 1B. It is possible in this aspect to show a increase in value from the first hue as compared to the resulting hue. In this example, the resulting hue is lighter than the initial hue.

Figure 3A:
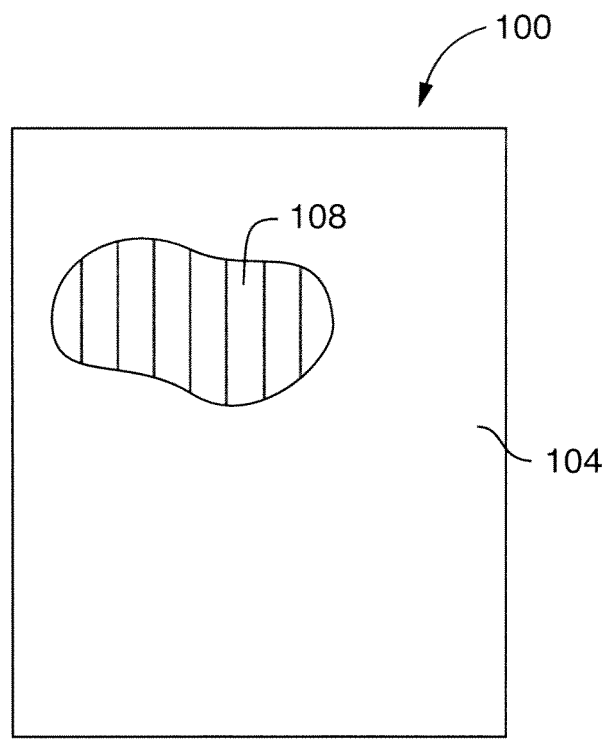
FIGS. 3A-B are schematic representations showing different indicator materials applied to different layers of a layered nonwoven substrate according to one aspect of the invention, and the change from one color to another after contact with a water-containing fluid.
Figure 3B:
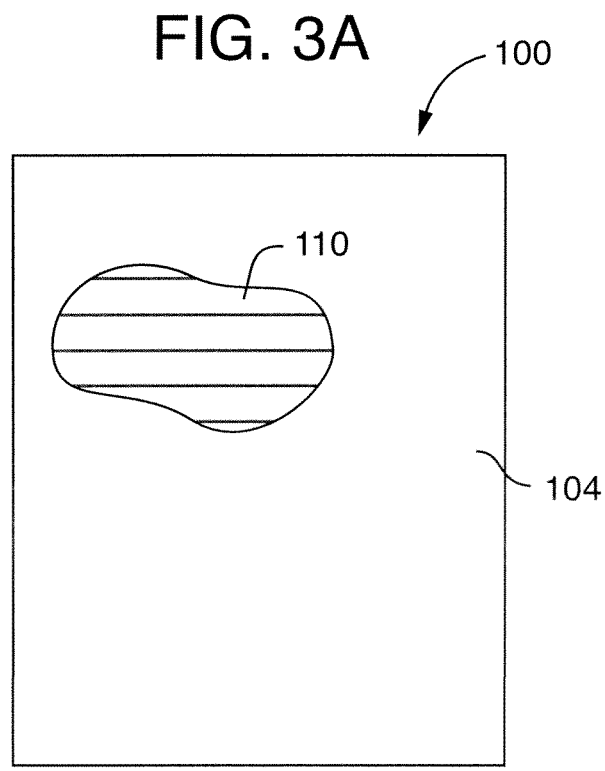
Figure 3C:
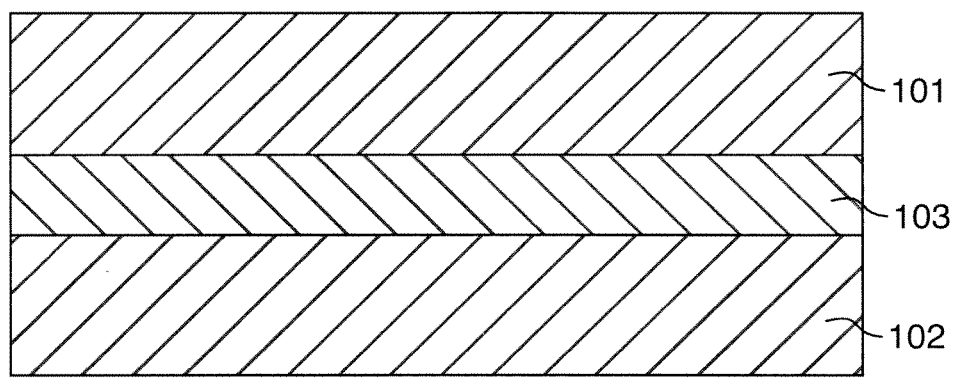
FIG. 3C is a cross-sectional view of the layered indicator material of FIGS. 3A-B.

An illustration of yet another aspect of the present sensor is presented in the series of schematic representations (photographs originally) shown in FIGS. 3A-3B. In this aspect there are three layers of material disposed on a substrate (see FIG. 3C). One layer 100 is an indicating material that changes from colored to colorless in the presence of a water-based liquid. This first indicating material is made from at least one leuco dye, a developer and a neutral surfactant. A second layer 102 is an indicating material of a different hue from that of the first. The second indicating material changes from colorless to colored in the presence of a water-based liquid. This second indicating material is made from at least one leuco dye, one desensitizer and one developer. The second layer 102 may be separated from the first dye layer by a third layer 104, as desired. The third layer 104 is a water soluble film or water permeable film that functions to prevent a reaction in the dry state between the first indicating material and the second indicating material.

For example, in FIG. 3A, the first layer indicating material (cyan dye) is deposited on a substrate and shows an initial cyan color in a dry state. FIG. 3B shows a change of a second layer indicating material from a cyan color to colorless after being exposed to a water-based liquid such as urine. This change is concomitant with the appearance of the second indicator material (magenta dye) also deposited on the substrate. The magenta dye goes from colorless to colored when exposed to the water-based liquid. In this particular aspect, the separation layer 104 is disposed between the cyan dye layer 100 and the magenta dye layer 102 so as to avoid a reaction between the two indicator materials. It is noted that the initial hue may have a higher, lower or equal value than the resulting hue.

According to the disclosure, suitable leuco dye agents include but are not limited to phthalide or fluoran type dyes. Phthalide type leuco dyes include arylmethane phthalides, such as triarylmethane phthalides and diarylmethane phthalides, monoheterocyclic substituted phthalides such as, heterocyclic substituted phthalides, diarylmethylazaphthalides, bisheterocyclic substituted phthalides, 3-heterocyclic substituted azaphthalides, 3,3-bisheterocyclic substituted azaphthalides, alkenyl substituted phthalides, bridged phthalides and bisphthalides. Specific examples of phthalide type leuco dyes include: 3,3-bis(p-dimethylaminophenyl)-6-dimethylaminophthalide; 3,3-bis(p-dimethylaminophenyl)phthalide; 3-(p-dimethylaminophenyl)-3-(1,2-dimethylindol-3-yl)phthalide; 3-(p-dimethylaminophenyl)-3-(2-methylindol-3-yl)phthalide; 3,3-bis(1,2-dimethylindol-3-yl)-5-dimethylaminophthalide; 3,3-bis(1,2-dimethylindol-3-yl)-6-dimethylaminophthalide; 3,3-bis(9-ethylcarbazol-3-yl)-6-dimethylaminophthalide; 3,3-bis(2-phenylindol-3-yl)-6-dimethylaminophthalide; 3-p-dimethylaminophenyl-3-(1-methylpyrrol-3-yl)-6-dimethylaminophthalide; 3,3-bis(1-n-butyl-2-methyl-3-indolyl)phthalide; 3,3-bis(4-diethylamino- 2-ethoxyphenyl)-4-azaphthalide and 3-(4-diethylamino-2-ethoxyphenyl)-3-(1-ethyl-2-methyl-3-indolyl)-4-azaphthalide.

Fluoran leuco dyes include 3',6'-dimethoxyfluoran; N-acetylauramine; N-phenylauramine; 3,6-dihexyloxyfluoran; 2'-chloro-6'-aminofluoran; 3,6-bis(diethylamino) fluoran-(4'-nitro)-anilinolactam; 2'-chloro-6'-diethylaminofluoran; rhodamine B lactam; 6-diethylamino-benzo[α]-fluoran; 2-(phenylimino ethanedilidene)-3,3-trimethyl-indoline; 3',6'-bis-(diphenylamino)fluoran; crystal violet lactone; benzoyl leucomethylene blue; ethyl leucomethylene blue; methoxybenzoyl leucomethylene blue; 2',6'-bis(diethyl-amino) fluoran; malachite green lactone; 2'-anilino-3' methyl-6'-(N-methyl-N-n-propylamino)fluoran; 3-cyclohexyl methylamino-6-methyl-7-anilinofluoran; 1,3,3-trimethyl-indolino-7'-chloro-β-naphthospiropyran and di-β-naphthospiropyran. The color-changing compositions of the invention include a leuco dye in an amount of from 0.1% to 10% of the total weight of the color-changing composition. Desirably, the color-changing compositions of the invention include a leuco dye in an amount of from 0.5% to 5% of the total weight of the color-changing composition. The color-changing compositions of the invention may include more than one leuco dye. One or more leuco dyes that have visually different colors may be combined or leuco dyes having the same visual color may be combined.

According to the disclosure, suitable developers include but are not limited to acid, weak acid, metal salt-based Lewis acids such as zinc chloride, zinc salicylates and aluminum chloride. The Lewis Acid is preferably a metal salt-based Lewis Acid. The salt of an aromatic carboxylic acid with polyvalent metals such as zinc, magnesium, aluminum, calcium, titanium, manganese, tin or nickel may also be used as the metal salt-based Lewis Acid. The metal salt based-Lewis Acid is preferably selected from zinc chloride, zinc salicylate, zinc nitrate, aluminum chloride, aluminum nitrate, aluminum sulfate, magnesium chloride and stannic chloride. Other examples of suitable developers include bisphenol A, phenol resins, 4-tert-butylphenol, α-naphthol, β-naphthol, 4-acetylphenol, 4-tert-octylphenol, 4,4'-sec-butylidenephenol, 4-phenylphenol, 4,4'-dihydroxydiphenylmethane, 4,4'-isopropylidene diphenol, hydroquinone, 4,4'-cyclohexylidene diphenol, 4,4-dihydroxy diphenylsulfide, 4,4'-thiobis (6-tert-butyl-3-methylphenol), 4,4'-dihydroxydiphenyl sulfone, hydroquinone monobenzyl ether, 4-hydroxybenzophenone, 2,4-dihydroxybenzophenone, 2,4,4'-trihydroxybenzophenone, 2,2',4,4'-tetrahydroxybenzophenone, dimethyl 4-hydroxyphthalate, methyl 4-hydroxybenzoate, ethyl 4-hydroxybenzoate, propyl 4-hydroxybenzoate, sec-butyl 4-hydroxybenzoate, pentyl 4-hydroxybenzoate, phenyl 4-hydroxybenzoate, benzyl 4-hydroxybenzoate, tolyl 4-hydroxybenzoate, chlorophenyl 4-hydroxybenzoate, phenylpropyl 4-hydroxybenzoate, phenethyl 4-hydroxybenzoate, p-chlorobenzyl 4-hydroxybenzoate, p-methoxybenzyl 4-hydroxybenzoate, novolak type phenol resins, phenol polymers and like phenol compounds.

According to the disclosure, the desensitizer can be any of known component agent which has good solubility in both water and organic solvents. The desensitizers can be neutral molecules that are without a charge, such as polyalkylene glycol of <1000 Daltons, polyalkylene oxide of <10000 Daltons, block copolymers of polyoxyethylene polyoxypropylene glycol, polyoxyethylene nonylphenyl ether, polyoxyethylene distyrenated phenyl ether, neutral surfactants.

Other examples of desensitizers may include glycerin; dodecylamine; 2,4,4-trimethyl-2-oxazoline; polyolefin glycols such as polyethylene glycol, polypropylene glycol and copolymer of ethylene glycol and propylene glycol; polyoxyethylene lauryl ether, polyoxyethylene oleyl ether, polyoxyethylene nonyl phenyl ether, polyoxyethylene sorbitan monolaurate, polyethylene glycol monostearate. The desensitizers can also be charged molecules, either negatively charged or positively charged. The desensitizers can also be zwitterionic with both negative charges and negative charges on the same molecules.

According to the disclosure, the surfactant may be a neutral surfactant or charged surfactants or zwitterionic surfactants. In some cases, neutral surfactants may be preferred. Suitable neutral surfactants include but are not limited to neutral block copolymer based surfactants that further include Pluronic series block copolymers, such as Pluronic P85 from BASF. Other examples of useful polymeric neutral surfactants include Tween 20, 40, 80 and Triton-x-100.

According to the disclosure, suitable binders include, but are not limited to compositions that consist of mainly organic soluble polymeric resins such as modified celluloses, polyesters and polyamides. Organic solvent based varnishes are also suitable binding compositions.

According to the disclosure, suitable solvents include but are not limited to volatile low alcohols such as ethanol, propanol and butanol. Other volatile solvents such as acetone, ethyl acetate, tetrahydrofuran and acetonitrile are also useful.

According to the disclosure, the standard colorants include any molecules and materials that have a hue that does not change upon wetting with urine and an aqueous medium. Examples of the standard colorants include, but not limited to, organic dyes, inorganic pigments, colored macromolecules, colored nanoparticles and materials. Examples of dyes include acridine dyes, anthraquinone dyes, arylmethane dyes, azo dyes, nitro dyes, nitroso dyes, phthalocyanine dyes, quinone-imine dyes, Aazin dyes, Indophenol dyes, oxazin dyes, Oxazone dyes, Thiazole dyes, xanthene dyes, Fluorene dyes, fluorone dyes, rhodamine dyes. Examples of pigments include Cadmium pigments: cadmium yellow, cadmium red, cadmium green, cadmium orange; Carbon pigments: carbon black (including vine blac, lamp black), ivory black (bone char); Chromium pigments: chrome yellow and chrome green; Cobalt pigments: cobalt violet, cobalt blue, cerulean blue, aureolin (cobalt yellow); Copper pigments: Azurite, Han purple, Han blue, Egyptian blue, Malachite, Paris green, Phthalocyanine Blue BN, Phthalocyanine Green G, verdigris, viridian; Iron oxide pigments: sanguine, caput mortuum, oxide red, red ochre, Venetian red, Prussian blue; Clay earth pigments (iron oxides): yellow ochre, raw sienna, burnt sienna, raw umber, burnt umber; Lead pigments: lead white, cremnitz white, Naples yellow, red lead; Mercury pigments: vermilion; Titanium pigments: titanium yellow, titanium beige, titanium white, titanium black; Ultramarine pigments: ultramarine, ultramarine green shade; Zinc pigments: zinc white, zinc ferrite. Other examples include alizarin, alizarin crimson, gamboge, cochineal red, rose madder, indigo, Indian yellow, Tyrian purple, organic quinacridone, magenta, phthalo green, phthalo blue, pigment red 170.

The standard colorant and the leuco dye can be applied generally over the entire substrate surface or at discrete localized spots on the substrate. They may further be printed in various shapes and sizes, graphics of patterns or alpha numeric symbols and/or words, or combinations thereof.

The useful substrates in the disclosure can vary. The substrates can be porous and hydrophobic films and sheet materials, or cellulosic-based substrates such as fiber fluff, paper tissues, paper sheets or towels and wipers. The substrates can also be nonporous plastic films and sheets, such as polyolefin films, or nonwoven materials. Examples of polyolefin films include polyethylene and polypropylene films, or modified polyethylene and polypropylene films. The substrates may be a part of an outer cover film of an absorbent article such as a diaper.

Wetness Sensors Containing at Least One pH Indicator and One Standard Colorant

In a different aspect of the disclosure, the wetness sensor may be made of a wider range of substrates and a color changing composition. The color-changing composition disposed on the substrate includes a matrix-forming component, at least one pH indicator, at least one standard colorant, at least one surfactant and at least one pH adjuster. The matrix-forming component can be a water-insoluble, film-forming polymer or a mixture of a number of polymers or an ink base/binder, such as a flexographic varnish having an organic solvent base. The pH indicator can be a charged pH indicator or a neutral pH indicator or a polymeric pH indicator that is capable of changing color in response to the change of pH. The standard colorant includes any molecules and materials that have a visual hue that does not change upon wetting by urine and aqueous medium. The surfactant includes neutral surfactants and charged surfactants. In some cases, it is desirable that the charged surfactants attract the oppositively charged pH indicator and/or standard colorants. The pH adjuster may include a low molecular weight organic acid and a high molecular weight organic acid.

When the multiple-component material is used as part of the outer cover component of a disposable diaper, the color-changing composition is in contact with the absorbent core of the diaper where fluid is stored during use. The color-changing composition may be applied as an ink to the substrate. The color-changing composition may be dissolved in an organic solvent that acts as a carrier that later evaporates after printing.

The color-changing compositions in this aspect of the present disclosure are fluid at room temperature and can be applied to a substrate without heating. For example, the color-changing composition may be printed as an ink onto a substrate at room temperature. The color-changing compositions of this particular aspect form a film-like layer when they are applied to a substrate and dried.

The color-changing compositions of this aspect of the disclosure may include an organic solvent as a vehicle for the compositions to be applied to a substrate where the organic solvent evaporates after application. When in the form of a film layer on a substrate, the color-changing compositions of the invention are wettable but insoluble in water. This feature makes the color-changing compositions desirable for use in articles where the compositions will be exposed to wetness.

As with a leuco-dye based ink, the printed layer may be formed on the substrate in a desired pattern.

The substrate that may be used in conjunction with this particular ink is broader in scope than that previously described. For instance, the substrate may be in the form of porous foam, reticulated foam, cellulose tissues, a plastic film, a woven material or a nonwoven material. Suitable plastic films that may be used to form the substrate include polyethylene films and polypropylene films. Suitable woven materials include woven materials made from natural fibers, synthetic fibers or combinations of natural and synthetic fibers. Natural fibers include cotton, silk and wool fibers and synthetic fibers include polyester, polyethylene and polypropylene fibers. Suitable nonwoven materials include nonwoven materials made through traditional techniques such as spunbond, meltblown and bonded carded web materials as described previously. The substrate may include combinations of the materials identified above such as a substrate that includes both the porous foam and a nonwoven material or a substrate that includes both a plastic film and a nonwoven material.

The multiple-component materials of this aspect include a printed layer that is adhered to the substrate. The printed layer includes a color-changing composition and standard colorant that unlike the color-changing composition, does not change in color when in contact with bodily fluids. The standard colorant is described supra.

The printed layer may be formed by the color-changing composition itself or the color-changing composition may be applied to or incorporated into the printed layer. Because the color-changing compositions of the invention are fluid at room temperature, they can be applied through printing or stamping either directly onto the substrate (thereby self-forming the printed layer) or onto a layer having a film-like structure and that is later associated with the substrate.

The color-changing composition includes a matrix-forming component which may include one or more water-insoluble, film-forming polymers and/or one or more ink-based materials. The matrix-forming component of the color-changing composition forms the medium to keep the colorant, the surfactant and pH adjuster in proximity to each other. This structure enables the performance of the color-changing composition to be wettable, but water-insoluble; and to remain as a film layer on the substrate as opposed to migrating/leaching away from the substrate.

The water-insoluble, film-forming polymers are solid at room temperature, but soluble in a volatile organic solvent or an organic mixing solvent so that when used, the color-changing composition is liquid at room temperature. The ink base materials are liquid at room temperature. When an ink base material is included in the matrix-forming component, a volatile organic solvent may or may not be used. Desirably, the water-insoluble, film-forming polymers/copolymers have a substantial amount, greater than about 0.5% by weight, of polar atoms such as oxygen and nitrogen. The polar atoms may be present in polar functional groups such as amides, carboxylic acids and esters.

Desirably, the water-insoluble polymers/copolymers are soluble in a volatile organic solvent such as ethanol, acetone, methanol, acetonitrile, tetrahydrofuran, benzene, toluene and mixtures of such solvents. The water-insoluble, film-forming polymer and the other components of the color-changing composition can be dissolved in the organic solvent prior to application onto the substrate. When the mixture of the color-changing composition and the organic solvent is formed, the mixture is liquid at room temperature. The volatile organic solvent evaporates when the color-changing composition is either applied to the printed layer or forms the printed layer.

The color-changing compositions of the invention include a matrix-forming component in an amount of from 20% to 95% of the total weight of the color-changing composition. Desirably, the color-changing compositions of the invention include a matrix-forming component in an amount of from 20% to 90% of the total weight of the color-changing composition.

Suitable water-insoluble, film-forming polymers include acrylate/acrylamide copolymers, polyurethane adhesives, copolymers of vinylpyrrolidone and copolymers of dimethyl aminopropyl methacrylamide. Commercially-available suitable polymers include DERMACRYL 79 polymer and AMPHOMER HC polymer, both of which are acrylate/octylacrylamide copolymers available from Akzo Nobel headquarted in Amsterdam, The Netherlands. Another example of a commercially-available suitable polymer is GANTREZ SP polymer, which is a monoalkyl ester of poly(methyl vinyl ether/maleic acid) copolymer available from International Specialty Products Inc. of Wayne, N.J.

Suitable ink base materials may be small molecules, polymeric materials or a mixture of small molecules and polymers. Examples of suitable small molecule base materials include glycols, including triglycerols and their derivatives. Examples of suitable polymeric materials that may be used as ink base materials include polyvinyl alcohol, polyvinyl pyrrolidone, polyethylene glycol, water-soluble derivatives of polyacrylates and polyacrylamides, poly(hydroxyethyl methacrylates), poly(hydroxylethyl acrylates), carboxymethyl cellulose, gelatin and gum Arabic. Another suitable ink base material for the color-changing compositions of the invention is a varnish base such as a nitrocellulose compound based varnish or a phenolic-modified co-solvent-type polyamide resin-based varnish. Further, the ink base material can be a flexographic varnish having an organic solvent base. It is believed that the ink base material may help the stability of the color-changing composition. It is also believed that the ink base material may improve the adhesion of the color-changing composition to the substrate of the multiple-component material. The ink base material may be water-soluble or water-insoluble.

The color-changing composition of this aspect also includes a pH indicator, preferably a charged pH indicator. The pH indicator may be a neutral pH indicator, a charged pH indicator or a zwitterionic pH indicator. The pH indicator desirably changes color at either a pH greater than 9.5 or a pH lower than 5.5. The color change may be from color to colorless, colorless to color or from one color to another color. The charged pH indicator has the charged functional groups either in the core chromophore structure or derivatized in pendent groups. The pH indicator may be derivatized as a polymer. Examples of suitable pH indicators include the following: gentian violet (methyl violet), leucomalachite green, methyl yellow, bromophenol blue, Congo red, methyl orange, malachite green, brillian green, crystal violet, erythrosin B, methyl green, methyl violet 2B, picric acid, napthol yellow S, quinaldine red, Eosin Y, basic fuchsin, 4-(p-anilinophenylazo)benzene-sulfonic acid, sodium salt, phloxine B, bromochlorophenol blue W.S., ethyl orange, bromocresol nile blue A, thymolphthalein, aniline blue W.S., alizarin yellow GG, morgant orange I, tropaeolin O, orange G, acid fuchsin, thiazol yellow G, indigo carmine, phenolphthalein, thymolphthalein, alizarine yellow R, bromocresol green and their respective derivatives. The color-changing compositions of the invention include a pH indicator in an amount of from 0.1% to 10% of the total weight of the color-changing composition. Desirably, the color-changing compositions of the invention include a pH indicator in an amount of from 0.5% to 5% of the total weight of the color-changing composition.

The color-changing compositions may include more than one colorant, and one or more standard colorants. One or more colorants that have visually different colors may be combined or colorants having the same visual color may be combined.

The color-changing formulation may include a neutral surfactant as described supra, or a charged surfactant. The surfactant may be a small molecule or a polymer. Suitable positively charged surfactants include benzathonium chloride and benzethonium chloride. Mixtures of positively charged surfactants may also be used. Suitable negatively charged surfactants include alkyl sulfates such as sodium laurylsulfate, sodium dodecylsulfate and sodium tetradodecyl sulfate. Alkylbenenesulfates such as sodium dodecylbenzene-sulfonate and sodium diheptylsulocuccinate are suitable negatively charged surfactants. Additional suitable negatively charged surfactants include dodecyltrimethyl ammonium chloride, stearateamine acetate, sodium polyoxyethyleneakyl ether sulfate and triethanolamine poly oxyethylenealkyl ether sulfate. Mixtures of negatively charged surfactants may also be used.

It is believed that the addition of a neutral surfactant to the color-changing composition will improve response speed by increasing the wettability of the color-changing composition. Using both the charged surfactants and a neutral surfactant improves response speed while maintaining the stability of the color-changing composition, particularly under high temperature and high humidity conditions. Suitable neutral surfactants include Tween 20, Tween 40, Tween 80, Triton-X-100, polyethylene lauryl ether, polyoxyethylene nonyl phenyl ether, polyoxyethylene oleyl phenyl ether, polyoxyethylene sorbitan monolaurate, polyethylene glycol monostearate, polyethylene glycol sorbitan monolaurate, polyoxyethylene sorbitan monopalmitate, polyoxyethylenesorbitan monostearate, polyoxyethylenesorbitan monooleate, polyoxyethylenesorbitan trioleate, polypropylene glycol sorbitan monolaurate, polyoxypropylenesorbitan monopalmitate, polyoxypropylenesorbitan monostearate, polyoxypropylenesorbitan monooleate, polyoxypropylenesorbitan trioleate, polyalkyne glycol sorbitan monolaurate, polyalkyne glycol sorbitan monopalmitate, polyalkyne glycol sorbitan monostearate, polyalkyne glycol sorbitan monooleate, polyalkyne glycol sorbitan trioleate and mixtures of such neutral surfactants.

The color-changing compositions of this aspect of the disclosure include surfactants in an amount of from 2% to 50% of the total weight of the color-changing composition. Desirably, the color-changing compositions of the invention include oppositely-charged surfactants in an amount of from 10% to 30% of the total weight of the color-changing composition. With regard to the relative amounts of the different types of surfactants, the ratio of charged surfactant to neutral surfactant can range from 0.2 to 10.

In addition to the other components in this aspect of the disclosure, the color-changing composition includes a pH adjuster. The pH adjuster is any molecule or composition that may be used to control the pH of the color-changing composition. The pH adjuster may be an acid, a base or a combination of both such as would be found with a buffering composition. The pH adjuster is selected in conjunction with the choice of colorant to be used in the color-changing composition. For example, if the color-changing composition includes a colorant that has a color transition point that occurs at a pH of lower than 5.5, the selected pH adjuster is desirably an acid to make the pH of the color-changing composition acidic. If the color-changing composition includes a colorant that transitions color at a pH higher than 9.5, the selected pH adjuster is desirably a base to make the pH of the color-changing composition basic.

When the substrate and printed layer combination of the multiple-component materials of the invention are used as part of the outer cover of an absorbent article, the pH adjuster component provides additional functionality. Absorbent articles having breathable and highly-breathable outer covers (that have the effect of drawing moisture and humidity away from the wearer's skin) have been commercially successful. The water-impermeable, film portion of the outer cover can be made "breathable" through incorporation of particles of calcium carbonate. When used in conjunction with a breathable outer cover material, the color-changing compositions of the invention desirably include a combination of a low molecular weight organic acid and a high molecular weight organic acid to prevent premature "activation" or a change in color by the colorant. When such a combination is used as the pH adjuster, migration of the acids into the outer cover film is mitigated, thereby preventing the premature activation of the colorant caused by a neutralization reaction between the acid and the calcium carbonate particles. The combination of a low molecular weight organic acid and a high molecular weight organic acid provides the best results; when a high molecular weight organic acid completely replaces the low molecular weight organic acid, the response time of the color-changing composition is relatively slower and the color contrast is not optimal. The low molecular weight organic acid typically has a molecular weight less than 1000 Daltons. The high molecular weight organic acid typically has a molecular weight greater than 1000 Daltons.

Examples of suitable acid pH adjusters include organic acids, inorganic acids and polymeric acids; more specifically, examples of low molecular weight organic acids include glycolic acid, citric acid, lactic acid, ascorbic acid, oxalic acid, maleic acid, tartaric acid, salicylic acid, palmitic acid and stearic acid. Examples of high molecular weight organic acids include polyacrylic acids, polymethacrylic acids and copolymers containing acrylic acids, methacrylic acids or both acrylic acids and methacrylic acids.

Both the low molecular weight acids and the high molecular weight acids can be "polymeric". Depending on the number of monomer units, the polymeric acid will either be low molecular weight (typically less than 1000 Daltons) or high molecular weight (typically greater than 1000 Daltons). The low molecular weight organic acids having repeating monomer units may be referred to as oligomers. In some aspects, the polymeric acid can be a "bidentate" or higher order acid. By "bidentate or higher order" it is meant that the polymeric acid has more than one acid group in its smallest polymer building block. This can be easily understood when one compares ascorbic acid to tartronic acid (two acid groups) and citric acid (three acid groups). In some aspects, the polymeric acids may be a dendrimer or the like where the dendrimer's surface and interior are fully functionalized with acid groups. Examples of suitable, simple polymeric acids for which the number of repeating monomer units can vary are salicylic acid and ascorbic acid; if the molecular weight is less than 1000 Daltons, the acid may be referred to as an oligomer and if the molecular weight is greater than 1000 Daltons, the acid may be referred to as a polymer. The following are examples of suitable dicarboxylic polymeric acids:

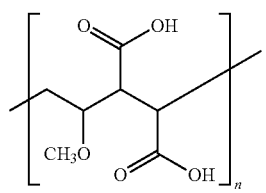

Poly(methyl vinyl ether-alt-maleic acid) average $M_w$~216,000 by LS, average $M_n$~80,000, powder -continued

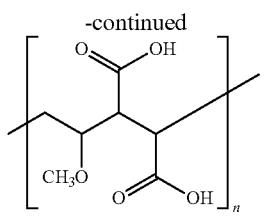

Poly(methyl vinyl ether-alt-maleic acid) average $M_w$~1,980,000 by LS, average $M_n$~960,000, powder Examples of suitable tricarboxylic polymeric acids include the following:

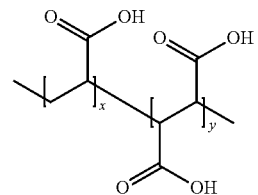

Poly(acrylic acid-co-maleic acid) solution average $M_w$ 3,000, 50 wt. % in $H_2O$ Examples of suitable polyacrylic acids include the following: polyacrylic acid having an average molecular weight of about 1800 Daltons, polyacrylic acid having an average molecular weight of about 450,000 Daltons, polyacrylic acid having an average molecular weight of about 1,250,000 Daltons and polyacrylic acid having an average molecular weight of about 3,000,000 Daltons. An example of a suitable, strong polymeric acid is Poly(vinylphosphonic acid).

Examples of suitable basic pH adjusters include organic bases, inorganic bases and polymeric bases; more specifically, examples include sodium hydroxide, sodium carbonate, sodium bicarbonate, sodium borate, potassium hydroxide, polymeric amines, dendrimeric amine and 1,3-pentanediamine. Combination pH adjusters that have a buffering effect include acetic buffer, borate buffer and carbonate buffer. Desirably, the pH of the combination pH adjuster is either greater than 10 or lower than 5. Typically, the combination pH adjuster is in solution form and the concentration of the buffer may range from about 0.01 milliMolar to about 1000 milliMolar and desirably range from about 1 milliMolar to about 20 milliMolar, depending on the combination pH adjuster selected. The color-changing compositions of the invention include a pH adjuster in an amount of from 0.1% to 20% of the total weight of the color-changing composition. Desirably, the color-changing compositions of the invention include a pH adjuster in an amount of from 0.5 to 5% of the total weight of the color-changing composition. With respect to the relative amounts of organic acid, the ratio of low molecular weight organic acid to high molecular weight organic acid can range from 0.02 to 50.

Benefits of the pH adjuster include stabilizing the colorant against premature color changes that may be caused by exposure to humid environments. For example, the pH adjuster is believed to maintain a stable pH, such as a low pH environment with an acidic pH adjuster, around the colorant even when the film layer is exposed to high humidity.

When the components of the color-changing composition are formed as a printed layer on the substrate, they can be dissolved or suspended in an organic solvent that later evaporates. The result of the color-changing composition forming a printed layer on the substrate is the multiple-component material of the invention. The organic solvent may be a single solvent or a mixture of solvents described supra.

An example of a useful application of the present invention is to apply the color-changing composition to a nonwoven substrate that is used as a component of a disposable absorbent article as described herein. However, this example is not meant to be limiting. The personal hygiene article may be a substrate that is not necessarily used with an absorbent material. The substrate may be tissue, nonwovens materials, paper, film and the like.

Wetness Sensors Containing Leuco Dyes and pH Indicators

It is contemplated that a color-changing composition can be made using the main aspects of this disclosure, namely the color changing composition having one or more leuco-dyes and pH indicators. This combined color changing composition includes at least the following components: a pH indicator; a surfactant; a pH adjuster, wherein the pH adjuster includes low molecular weight organic acid and a high molecular weight organic acid, and a leuco dye and a developer. Each such component is described supra. The components may be combined as long as they are compatible with one another.

In accordance with the present disclosure, one or more sensors described herein can also be integrated into an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underzones, bedzones, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

The indicating material is on a layer of the substrate that is either on a top sheet of the substrate or within an undersheet that is visible to a caregiver. The indicating material further contains a wettability enhancing agent, or a hydrophilic water-soluble agent. The indicating material is applied either at discrete localized spots on the surface of said substrate or generally over the entire substrate surface. Alternatively, the indicating materials are printed in different patterns and shapes on the substrate. The substrate can be printed with multiple indicating materials on different portions of the substrate.

The wetness sensor may be composed of a solid substrate on which a colored chemical composition is deposited. The solid substrate can be any substrate that allows a deposition of the indicator composition to exhibit a color. The solid substrates may be porous or may not be porous. Examples of the solid substrate include, but not limited to, porous tissues, papers, polymeric films, metals, wood, plastics, rubbers, nonwoven materials and woven materials.

Typically, for consumer-related health and hygiene products, the sensor substrate can be made from a polyolefin, such as a plastic film consisting of polyethylene film and polypropylene film. The sensor substrate also can be made in part with cellulose-based sheets. According to an alternate embodiment for an absorbent product, such as feminine pads or tampons, may contain one or more of the wetness sensors to show the insult of the absorbent product by menses or vaginal fluids. The sensors become colorless in the presence of a liquid sample containing a significant portion of water molecules. As stated before, the colored chemical composition has at least one electron-rich leuco dye and one electron deficient acceptor. The wetness sensor becomes colorless upon contact with a liquid containing a sufficient amount of water.

Various embodiments of an absorbent article that can be formed according to the present disclosure will now be described in more detail. Only for purposes of further explaining the inventive concept, an absorbent article in the embodiment of a training pant will be used as an example. It should be understood, however, that the other absorbent articles previously mentioned could be used.

Generally speaking, the sensors of the present disclosure can be incorporated into the absorbent article in a variety of different orientations and configurations, so long as the sensor is capable of receiving bodily fluids or waste (e.g., urine and/or fecal material) and providing a signal to a user or caregiver regarding the presence or absence of urine. The indicating materials containing the standard colorant and leuco dye can directly be immobilized or printed on a portion of the inner side of the outer cover film of the article in different shapes and patterns. The indicating materials can also be immobilized or printed on a piece of substrate to make a wetness sensor of different patterns which is sandwiched between the outer cover film and the superabsorbent materials of the article. Each portion of the patterns and shapes may be made of the indicating materials of different colors.

For example, sensor can be visible to the user or caregiver so that a simple, accurate, and rapid indication of wetness can be provided. The visibility can be accomplished in a variety of ways. For example, in some embodiments, the absorbent article can include a transparent or translucent portion (e.g., window, film, etc.) that allows the sensor to be readily viewed without removal of the absorbent article from the wearer and/or without disassembly of the absorbent article. In other embodiments, the sensor can extend through a hole or aperture in the absorbent article for observation. In still other embodiments, the sensor can simply be positioned on a surface of the absorbent article for observation.

Regardless of the particular manner in which it is integrated, urine can be directly discharged to a portion of the sensor, a liquid permeable cover or other material surrounding the sensor, or can be discharged onto a component of the absorbent article into which the sensor has been integrated.

Exemplary Absorbent Article

The wetness sensor is useful in disposable absorbent articles such as pants, diapers and pads. An absorbent article of the present invention generally can have an absorbent core, and can optionally include a topsheet and/or a backsheet, where the absorbent core can be disposed between the topsheet and the backsheet. To gain a better understanding of the present invention, attention is directed to FIGS. 1 and 2 for exemplary purposes showing a training pant and a signal composite of the present invention.

Various materials and methods for constructing training pants are disclosed in U.S. Pat. No. 6,761,711 to Fletcher et al.; U.S. Pat. No. 4,940,464 to Van Gompel et al.; U.S. Pat. No. 5,766,389 to Brandon et al., and U.S. Pat. No. 6,645,190 to Olson et al., each of which is incorporated herein by reference in a manner that is consistent herewith.

Figure 4:
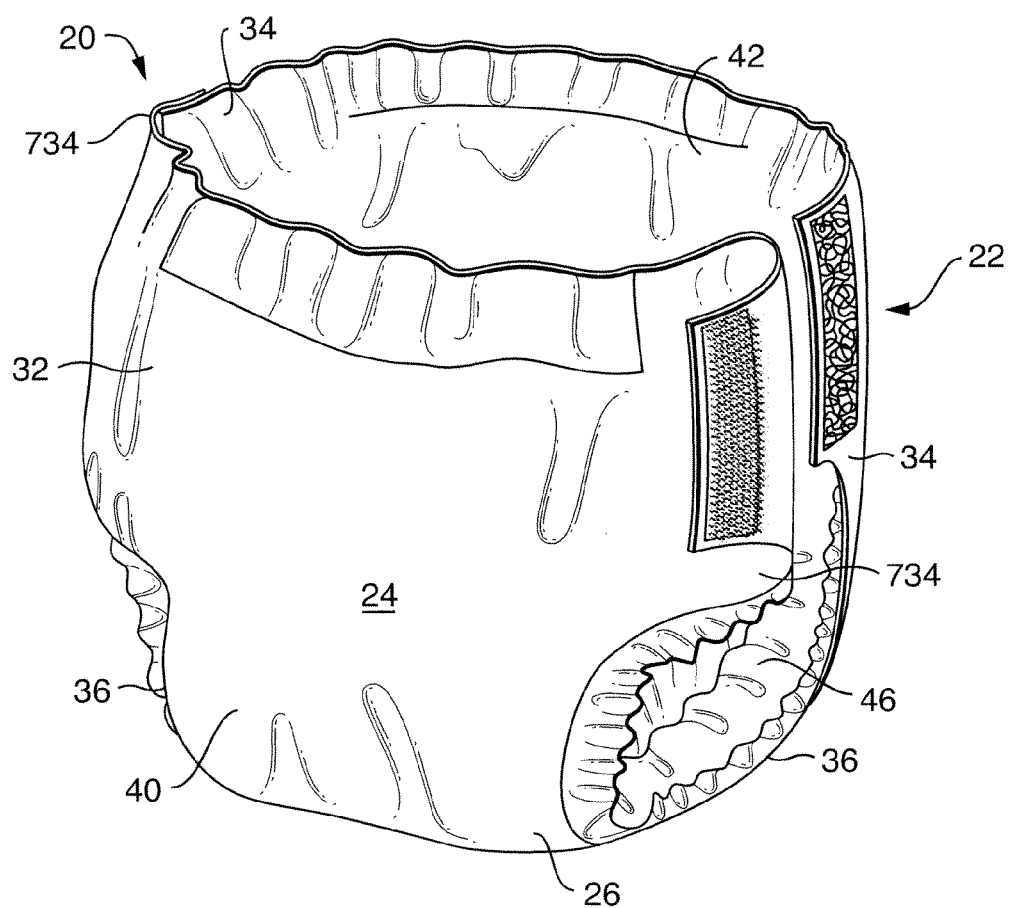
FIG. 4 is a front perspective view of one embodiment of an absorbent article.
Figure 5:
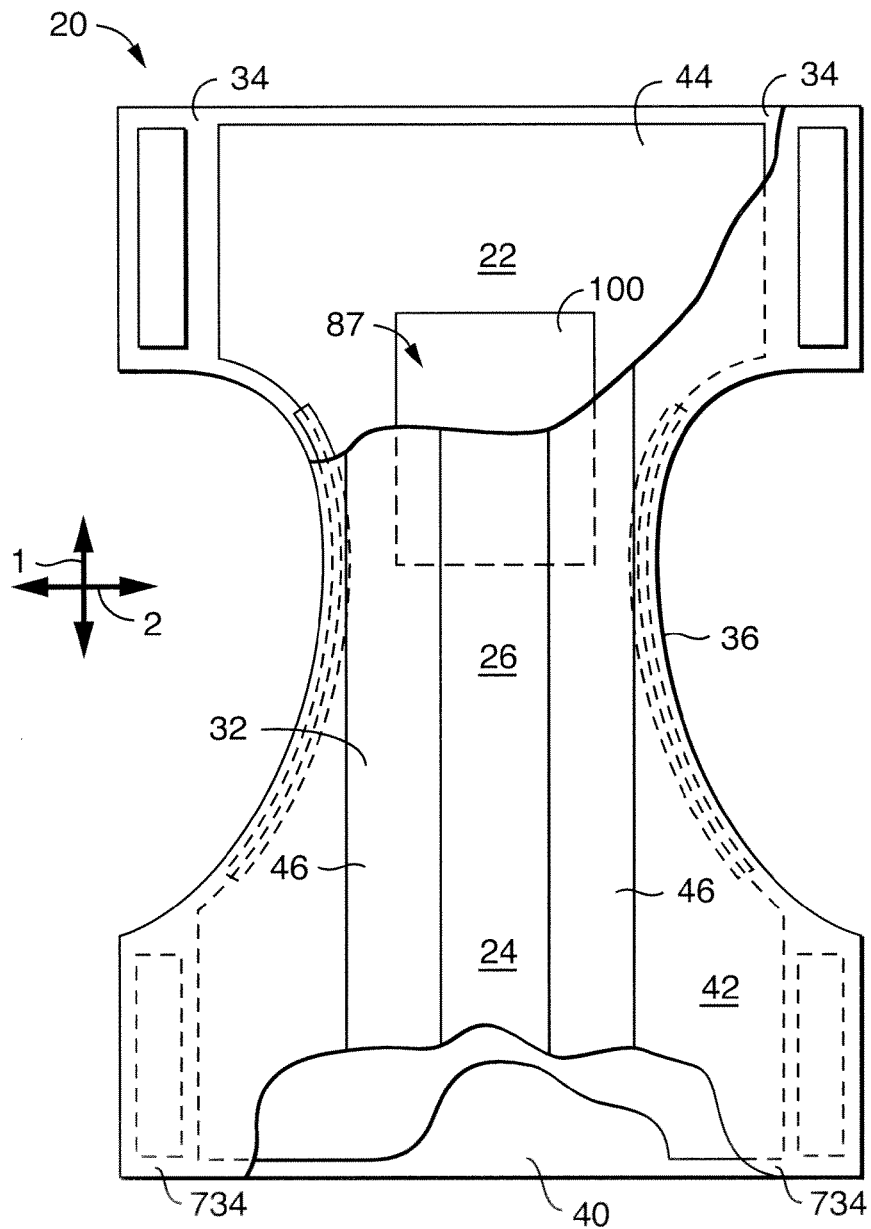
FIG. 5 is a plan view of the absorbent article of FIG. 4, as unfastened, unfolded, and laid out flat.

FIG. 4 illustrates a training pant 20 in a partially fastened condition, and FIG. 5 illustrates a training pant 20 in an opened and unfolded state. The training pant 20 defines a longitudinal direction 1 that extends from the front of the training pant when worn to the back of the training pant. Perpendicular to the longitudinal direction 1 is a lateral direction 2.

The training pant 20 defines a front region 22, a back region 24, and a crotch region 26 extending longitudinally between and interconnecting the front and back regions. The pant 20 also defines an inner surface (i.e., body-facing surface) adapted in use (e.g., positioned relative to the other components of the pant) to be disposed toward the wearer, and an outer surface (i.e., garment-facing surface) opposite the inner surface. The training pant 20 has a pair of laterally opposite side edges and a pair of longitudinally opposite waist edges.

The illustrated pant 20 may include a chassis 32, a pair of laterally opposite front side panels 34 extending laterally outward at the front region 22 and a pair of laterally opposite back side panels 734 extending laterally outward at the back region 24. The pant 20 further includes a sensor 100 that is placed, for example, between the absorbent core 44 and the topsheet 42 so that the sensor surface 87 is revealed from the inside of the pant 20. In an alternative (not shown), the sensor 100 is located between the backsheet 40 and the absorbent core 44 so that it may be viewed through the backsheet. Sensor 100 may be located anywhere on the absorbent article where wetness sensing is desired.

The chassis 32 includes a backsheet 40 and a topsheet 42 that may be joined to the backsheet 40 in a superimposed relation therewith by adhesives, ultrasonic bonds, thermal bonds or other conventional techniques. The chassis 32 may further include an absorbent core 44 such as shown in FIG. 2 disposed between the backsheet 40 and the topsheet 42 for absorbing fluid body exudates exuded by the wearer, and may further include a pair of containment flaps 46 secured to the topsheet 42 or the absorbent core 44 for inhibiting the lateral flow of body exudates.

The backsheet 40, the topsheet 42 and the absorbent core 44 may be made from many different materials known to those skilled in the art. The backsheet 40 may be constructed of a nonwoven material. The backsheet 40, may be a single layer of a fluid impermeable material, or alternatively may be a multi-layered laminate structure in which at least one of the layers is fluid impermeable.

Examples of suitable backsheet 40 materials are spunbond-meltblown fabrics, spunbond-meltblown-spunbond fabrics, spunbond fabrics, or laminates of such fabrics with films, or other nonwoven webs; elastomeric materials that may include cast or blown films, meltblown fabrics or spunbond fabrics composed of polyethylene, polypropylene, or polyolefin elastomers, as well as combinations thereof. The backsheet 40 may include materials that have elastomeric properties through a mechanical process, printing process, heating process or chemical treatment. For example, such materials may be apertured, creped, neck-stretched, heat activated, embossed, and micro-strained, and may be in the form of films, webs, and laminates.

One example of a suitable material for a biaxially stretchable backsheet 40 is a breathable elastic film/nonwoven laminate, such as described in U.S. Pat. No. 5,883,028, to Morman et al., incorporated herein by reference in a manner that is consistent herewith. Examples of materials having two-way stretchability and retractability are disclosed in U.S. Pat. No. 5,116,662 to Morman and U.S. Pat. No. 5,114,781 to Morman, each of which is incorporated herein by reference in a manner that is consistent herewith.

The topsheet 42 is suitably compliant, soft-feeling and non-irritating to the wearers skin. The topsheet 42 is also sufficiently liquid permeable to permit liquid body exudates to readily penetrate through its thickness to the absorbent core 44. A suitable topsheet 42 may be manufactured from a wide selection of web materials, such as porous foams, reticulated foams, apertured plastic films, woven and non-woven webs, or a combination of any such materials. For example, the topsheet 42 may include a meltblown web, a spunbonded web, or a bonded-carded-web composed of natural fibers, synthetic fibers or combinations thereof. The topsheet 42 may be composed of a substantially hydrophobic material, and the hydrophobic material may optionally be treated with a surfactant or otherwise processed to impart a desired level of wettability and hydrophilicity.

The topsheet 42 may also be extensible and/or elastomerically extensible. Suitable elastomeric materials for construction of the topsheet 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon, a business having offices located in Cleveland, Ohio U.S.A.), or PEBAX elastomers. The topsheet 42 can also be made from extensible materials such as those described in U.S. Pat. No. 6,552,245 to Roessler et al. which is incorporated herein by reference in a manner that is consistent herewith. The topsheet 42 can also be made from biaxially stretchable materials as described in U.S. Pat. No. 6,969,378 to Vukos et al. which is incorporated herein by reference in a manner that is consistent herewith.

The article 20 can optionally further include a surge management layer which may be located adjacent the absorbent core 44 and attached to various components in the article 20 such as the absorbent core 44 or the topsheet 42 by methods known in the art, such as by using an adhesive. Examples of suitable surge management layers are described in U.S. Pat. No. 5,486,166 to Bishop et al.; U.S. Pat. No. 5,490,846 to Ellis et al.; and U.S. Pat. No. 5,820,973 to Dodge et al., each of which is incorporated herein by reference in a manner that is consistent herewith.

The article 20 can further comprise an absorbent core 44. The absorbent core 44 may have any of a number of shapes. For example, it may have a 2-dimensional or 3-dimensional configuration, and may be rectangular shaped, triangular shaped, oval shaped, race-track shaped, I-shaped, generally hourglass shaped, T-shaped and the like. It is often suitable for the absorbent core 44 to be narrower in the crotch portion 26 than in the rear 24 or front 22 portion(s). The absorbent core 44 can be attached in an absorbent article, such as to the backsheet 40 and/or the topsheet 42 for example, by bonding means known in the art, such as ultrasonic, pressure, adhesive, aperturing, heat, sewing thread or strand, autogenous or self-adhering, hook-and-loop, or any combination thereof.

The absorbent core 44 can be formed using methods known in the art. While not being limited to the specific method of manufacture, the absorbent core can utilize forming drum systems, for example, see U.S. Pat. No. 4,666,647 to Enloe et al., U.S. Pat. No. 4,761,258 to Enloe, U.S. Pat. No. 6,630,088 to Venturino et al., and U.S. Pat. No. 6,330,735 to Hahn et al., each of which is incorporated herein by reference in a manner that is consistent herewith. Examples of techniques which can introduce a selected quantity of optional superabsorbent particles into a forming chamber are described in U.S. Pat. No. 4,927,582 to Bryson and U.S. Pat. No. 6,416,697 to Venturino et al., each of which is incorporated herein by reference in a manner that is consistent herewith.

In some desirable aspects, the absorbent core includes cellulose fiber and/or synthetic fiber, such as meltblown fiber, for example. Thus, in some aspects, a meltblown process can be utilized, such as to form the absorbent core in a coform line. In some aspects, the absorbent core 44 can have a significant amount of stretchability.

The absorbent core 44 can additionally or alternatively include absorbent and/or superabsorbent material. Accordingly, the absorbent core 44 can comprise a quantity of superabsorbent material and optionally fluff contained within a matrix of fibers. In some aspects, the total amount of superabsorbent material in the absorbent core 44 can be at least about 10% by weight of the core, such as at least about 30%, or at least about 60% by weight or at least about 90%, or between about 10% and about 98% by weight of the core, or between about 30% to about 90% by weight of the core to provide improved benefits. Optionally, the amount of superabsorbent material can be at least about 95% by weight of the core, such as up to 100% by weight of the core. In other aspects, the amount of absorbent fiber of the present invention in the absorbent core 44 can be at least about 5% by weight of the core, such as at least about 30%, or at least about 50% by weight of the core, or between about 5% and 90%, such as between about 10% and 70% or between about 10% and 50% by weight of the core. In still other aspects, the absorbent core 44 can optionally comprise about 35% or less by weight unmodified fluff, such as about 20% or less, or 10% or less by weight unmodified fluff.

It should be understood that the absorbent core 44 is not restricted to use with superabsorbent material and optionally fluff. In some aspects, the absorbent core 44 may additionally include materials such as surfactants, ion exchange resin particles, moisturizers, emollients, perfumes, fluid modifiers, odor control additives, and the like, and combinations thereof. In addition, the absorbent core 44 can include foam.

EXAMPLES

Color changing ink was made by mixing leuco and non-leuco dyes with developers and desensitizers. The ink was then coated onto propylene film. At a dry state (about 50% humidity), the ink on the substrate is one hue, but changes to a different hue when exposed to water or urine. Solution A contains leuco dye, Crystal Violet Lactone (CVL) 0.0367 g, developers Zinc Salicylate 0.0123 g and Propyl Gallate 0.0624 g in 1 ml of acetone. Next, Betaine was dissolved in ethanol at 80 mg/ml, Bromothymol Blue was dissolved in ethanol at 6 mg/ml, Methyl Red was dissolved in acetone at 3 mg/ml, and Malachite Green was dissolved in acetone at 0.8 mg/ml.

Example 1

Solution a was mixed with the Betaine solution and the Bromothymol Blue in 25:40:20 ratios. The solution was then coated with a pipette tip onto a polypropylene film. After the coating was dried, the film was yellow. Once a drop of water was put on top of the film, the water spot immediately changed to blue. The blue color was completely immobilized on the film, therefore no leaching was detected.

Example 2

Solution A was mixed with the Betaine solution and the Methyl Red in 25:40:4 ratios. The solution was then coated with a pipette tip onto the polypropylene film. After the coating was dried, the film was pink-red. Once a drop of water was put on top of the film, the water spot immediately changed to purple-blue. The purple-blue dye was completely immobilized on the film, therefore no leaching was detected.

Example 3

Solution A was mixed with the Betaine solution and the Malachite Green in 25:40:5 ratios. The solution was then coated with a pipette tip onto the polypropylene film. After the coating was dried, the film was light green. Once a drop of water was put on top of the film the water spot immediately changed to blue. The blue dye was completely immobilized on the film, therefore no leaching was detected.

The present disclosure has been described in general and in detail by means of examples. Persons of skill in the art understand that the disclosure is not limited necessarily to the embodiments specifically disclosed, but that modifications and variations may be made without departing from the scope of the disclosure as defined by the following claims or their equivalents, including other equivalent components presently known, or to be developed, which may be used within the scope of the present disclosure. Therefore, unless changes otherwise depart from the scope of the disclosure, the changes should be construed as being included herein.

The invention claimed is:

1. A sensor for detecting the presence of an aqueous-based liquid in a personal hygiene article, the sensor comprising:
   a first layer comprising a first wetness indicating material adapted to change from colored to colorless when in contact with an aqueous liquid, the first wetness indicating material having a first hue; and
   a second layer comprising a second wetness indicating material adapted to change from colorless to colored when in contact with an aqueous liquid, the second wetness indicating material having a second hue;
   wherein the first hue and the second hue are two secondary colors, two primary colors, or an unrelated primary and secondary color.

2. The sensor according to claim 1, wherein the first wetness indicating material or the second wetness indicating material comprises a leuco dye that is selected from the group consisting of fluoran-type leuco dyes, phthalide-type leuco dyes, monoheterocyclic substituted phthalides, diarylmethylazaphthalides, bisheterocyclic substituted phthalides3, heterocyclic substituted azaphthalides, 3,3-bisheterocyclic substituted azaphthalides, alkenyl substituted phthalides, bridged phthalides, and bisphthalides.

3. The sensor according to claim 2 wherein the first and/or second wetness indicating material further comprises at least one developer.

4. The sensor according to claim 2 wherein the first and/or second wetness indicating material further comprises at least one desensitizer.

5. The sensor according to claim 2 wherein the first and/or second wetness indicating material further includes at least one neutral surfactant.

6. The sensor according to claim 1 wherein the first and/or second wetness indicating material comprises at least one pH indicating dye that is selected from the group consisting of gentian violet (methyl violet), leucomalachite green, methyl yellow, bromophenol blue, Congo red, methyl orange, malachite green, brillian green, crystal violet, erythrosin B, methyl green, methyl violet 2B, picric acid, napthol yellow S, quinaldine red, Eosin Y, basic fuchsin, 4-(p-anilinophenylazo)benzene-sulfonic acid, sodium salt, phloxine B, bromochlorophenol blue W.S., ethyl orange, bromocresol nile blue A, thymolphthalein, aniline blue W.S., alizarin yellow GG, morgant orange I, tropaeolin O, orange G, acid fuchsin, thiazol yellow G, indigo carmine, phenolphthalein, thymolphthalein, alizarine yellow R, bromocresol green and their respective derivatives.

7. The sensor according to claim 1 wherein the first and/or second wetness indicating material further includes a charged surfactant.

8. The sensor according to claim 1 wherein the first and/or second wetness indicating material further includes a pH adjuster, wherein the pH adjuster comprises a low molecular weight organic acid and a high molecular weight organic acid.

9. The sensor according to claim 1 wherein the first and/or second wetness indicating material further includes a matrix-forming component.

10. The sensor according to claim 1 wherein the first hue has the same hue as the second hue.

11. The sensor according to claim 1 wherein the first hue is higher in value than the second hue.

12. The sensor according to claim 1 wherein the first hue is the same in value as the second hue.

13. The sensor according to claim 1 wherein the first and second wetness indicating material is in the form of a liquid formulated to be disposed on the substrate by printing.

14. An absorbent article comprising a sensor according to claim 1.

15. The sensor of claim 1 further comprising a third layer separating the first layer from the second layer.

16. The sensor of claim 15 wherein the third layer comprises a water soluble film.

17. A sensor for detecting the presence of an aqueous-based liquid in a personal hygiene article, the sensor comprising:
   a first layer comprising a first wetness indicating material adapted to change from colored to colorless when in contact with an aqueous liquid;
   a second layer comprising a second wetness indicating material adapted to change from colorless to colored when in contact with an aqueous liquid; and
   at third layer comprising a water soluble film separating the first layer from the second layer.

* * * * *